US012673087B2

(12) United States Patent
Lantz et al.

(10) Patent No.: US 12,673,087 B2
(45) Date of Patent: Jul. 7, 2026

(54) MUCOSAL-ASSOCIATED INVARIANT T (MAIT) CELLS EXPRESSING CHIMERIC ANTIGEN RECEPTORS

(71) Applicants: INSERM (INSTITUT NATIONAL DE LA SANTÉ ET DE LA RECHERCHE MÉDICALE), Paris (FR); UNIVERSITÉ PARIS CITÉ, Paris (FR); ASSISTANCE PUBLIQUE-HÔPITAUX DE PARIS (APHP), Paris (FR); INSTITUT CURIE, Paris Cedex (FR)

(72) Inventors: Olivier Lantz, Paris (FR); Sophie Caillat-Zucman, Paris (FR)

(73) Assignees: INSERM (Institut National de la Santé et de la Recherche Médicale, Paris (FR); Université de Paris, Paris (FR); ASSISTANCE PUBLIQUE-HÔPITAUX DE PARIS (APHP), Paris (FR); INSTITUT CURIE, Paris (FR)

( * ) Notice: Subject to any disclaimer, the term of this patent is extended or adjusted under 35 U.S.C. 154(b) by 1113 days.

(21) Appl. No.: 17/414,689

(22) PCT Filed: Dec. 18, 2019

(86) PCT No.: PCT/EP2019/085998
§ 371 (c)(1),
(2) Date: Jun. 16, 2021

(87) PCT Pub. No.: WO2020/127513
PCT Pub. Date: Jun. 25, 2020

(65) Prior Publication Data
US 2022/0016171 A1      Jan. 20, 2022

(30) Foreign Application Priority Data
Dec. 18, 2018    (EP) .................................... 18306743

(51) Int. Cl.
| | |
|---|---|
| *A61K 35/28* | (2015.01) |
| *A61K 35/00* | (2006.01) |
| *A61K 35/17* | (2025.01) |
| *A61K 38/17* | (2006.01) |
| *A61K 40/11* | (2025.01) |
| *A61K 40/31* | (2025.01) |
| *A61K 40/42* | (2025.01) |
| *A61P 31/00* | (2006.01) |
| *A61P 33/00* | (2006.01) |
| *A61P 35/00* | (2006.01) |
| *A61P 35/02* | (2006.01) |
| *A61P 37/02* | (2006.01) |
| *C07K 14/705* | (2006.01) |
| *C12N 5/0783* | (2010.01) |

(52) U.S. Cl.
CPC .......... *A61K 38/1774* (2013.01); *A61K 35/28* (2013.01); *A61K 40/11* (2025.01); *A61K 40/31* (2025.01); *A61K 40/428* (2025.01); *A61P 35/00* (2018.01); *C12N 5/0636* (2013.01)

(58) Field of Classification Search
None
See application file for complete search history.

(56) References Cited

U.S. PATENT DOCUMENTS

2017/0281683 A1 * 10/2017 Heczey ............. C07K 14/7051

FOREIGN PATENT DOCUMENTS

| WO | WO-2017040945 A1 * | 3/2017 | ............. A61K 35/17 |
| WO | WO-2017180989 A2 * | 10/2017 | ......... A61K 39/4611 |
| WO | WO-2018044866 A1 * | 3/2018 | ............. A61K 35/17 |

OTHER PUBLICATIONS

Gherardin et al. Enumeration, functional responses and cytotoxic capacity of MAIT cells in newly diagnosed and relapsed multiple myeloma. Scientific Reports. 8: 4159; Published: Mar. 7, 2018 (Year: 2018).*
Guo et al. Immunotherapy of non-Hodgkin's lymphoma with a defined ratio of CD8+ and CD4+ CD19-specific chimeric antigen receptor-modified T cells. Frontiers in Immunology. 6: 247; Published: May 20, 2015 (Year: 2015).*
NIH's Dictionary of Cancer Terms—Immunocompromised (Year: 2024).*
Lee et al. Long-Term Outcomes Following CD19 CAR T Cell Therapy for B-ALL are Superior in Patients Receiving a Fludarabine/ Cyclophosphamide Preparative Regimen and Post-CAR Hematopoietic Stem Cell Transplantation. Blood. 128(22): 218; Published: Dec. 2, 2016 (Year: 2016).*
Turtle et al. Immunotherapy of non-Hodgkin's lymphoma with a defined ratio of CD8+ and CD4+ CD19-specific chimeric antigen receptor-modified T cells. Science Translational Medicine. 8: 355; Published: Sept 7, 2016 (Year: 2016).*
Trottein et al. Reengineering chimeric antigen receptor T cells for targeted therapy of autoimmune disease. Frontier in Immunology. 9: 1750; Published: Aug. 2, 2018 (Year: 2018).*

(Continued)

*Primary Examiner* — Daniel E Kolker
*Assistant Examiner* — Katherine Ann Holtzman
(74) *Attorney, Agent, or Firm* — WCF IP

(57) ABSTRACT

The present invention relates generally to immunotherapy, in particular immunotherapy for treating cancer, infectious diseases or autoimmune diseases. More specifically, the invention relates to Mucosal-Associated Invariant T (MAIT) cells expressing Chimeric Antigen Receptors (CARs), wherein the MAIT cell is allogenic with respect to the subject to be treated.

16 Claims, 4 Drawing Sheets
Specification includes a Sequence Listing.

(56) References Cited

OTHER PUBLICATIONS

Ellebrecht et al. Reengineering chimeric antigen receptor T cells for targeted therapy of autoimmune disease. Science. 353(6295): 179-184; Published: Jun. 30, 2016 (Year: 2016).*

Wang et al. Phase 1 studies of central memory-derived CD19 CAR T-cell therapy following autologous HSCT in patients with B-cell NHL. Blood. 127(24): 2980-2990; Published: Jun. 16, 2016 (Year: 2016).*

Wakao et al. Mucosal-Associated Invariant T cells in Regenerative Medicine. Frontiers in Immunology. 8: 1711; Published: Dec. 1, 2017 (Year: 2017).*

Rafiq et al. Optimized T-cell receptor-mimic chimeric antigen receptor T cells directed toward the intracellular Wilms Tumor 1 antigen. Leukemia. 31: 1788-1797; Published: Jan. 3, 2017 (Year: 2017).*

Cipriani et al. Autoimmunity in atopic dermatitis: Biomarker or simply epiphenomenon? Journal of Dermatology. 41: 569-576; Published: May 8, 2014 (Year: 2014).*

Hu et al. Anti-IgE therapy for IgE-mediated allergic diseases: from neutralizing IgE antibodies to eliminating IgE+ B cells. Clinical and Translational Allergy. 8: 27; Published: Jul. 18, 2018 (Year: 2018).*

Maus et al. T Cells Expressing Chimeric Antigen Receptors Can Cause Anaphylaxis in Humans. Cancer Immunology Research. 1: 26-31; Published: Jul. 10, 2013 (Year: 2013).*

Varelias et al. The Journal of Clinical Investigation. 128(5): 1919-1936; Published: Feb. 16, 2018 (Year: 2018).*

Kanda et al. International Journal of Hematology. 98: 300-308; Published: Jul. 28, 2013 (Year: 2013).*

Graham et al:"Allogeneic CAR-T Cells: More than Ease of Access?", Cells, vol. 7, No. 10, Oct. 1, 2018.

Lantz et al: "MAIT cells: an historical and evolutionary perspective", Immunology and Cell Biology, vol. 96, No. 6, pp. 564-572, Jul. 2018.

Leyfman: "Chimeric antigen receptors: unleashing a new age of anti-cancer therapy", Cancer Cell International, vol. 18, Nov. 14, 2018.

Qasim et al: "Molecular remission of infant B-ALL after infusion of universal TALEN gene-edited CAR T cells", Science Translational Medicine, vol. 9, Jan. 25, 2017.

Rudak et al: "MAIT cell-mediated cytotoxicity: Roles in host defense and therapeutic potentials in infectious diseases and cancer", Journal of Leukocyte Biology, vol. 104, No. 3, pp. 473-486, Sep. 2018.

Salou et al: "MAT cells in infectious diseases", Current Opinion in Immunology, vol. 48, pp. 7-14, Jul. 24, 2017.

* cited by examiner xeno-GvHD mice

MUCOSAL-ASSOCIATED INVARIANT T (MAIT) CELLS EXPRESSING CHIMERIC ANTIGEN RECEPTORS

FIELD OF THE INVENTION

The present invention relates generally to immuno-therapy, in particular immunotherapy for treating cancer, infectious diseases or autoimmune diseases. More specifi-cally, the invention relates to Mucosal-Associated Invariant T (MATT) cells expressing Chimeric Antigen Receptors (CARs).

BACKGROUND OF THE INVENTION

Immunotherapy using T cells expressing chimeric antigen receptors (CAR-T) has shown remarkable clinical results in the treatment of leukemia and is one of the most promising new strategies to treat cancer and other diseases such as infections or autoimmunity. Among the most successful CARs used to date are those targeting CD19, which offer the prospect of complete remissions in patients with relapsed or treatment-refractory hematological malignancies. CAR-T cell therapy represents an immunotherapy whereby lympho-cytes are genetically modified to express a CAR that allows recognition of a specific antigen. Upon antigen recognition, these modified T cells are activated via signaling domains converting them into potent cell killers. Current clinical protocols mainly utilize autologous T cells that are collected from a patient by apheresis, genetically modified to express the CAR, cultured in vitro in order to amplify the number of cells and finally re-infused back to the same patient. This approach requires patient-specific cell manufacturing, which unavoidably results in patient-to-patient variability in the final cell product, with variable potency and safety. This approach based on autologous cell transfer has other draw-backs such as the production time (around 2 months between apheresis and re-infusion). This delay is critical, as certain patients face vital emergency. In addition, immune cells from sick patients may be poorly functional or present in very low numbers. Therefore, such treatment using the patient's own lymphocytes is costly, time-consuming and is not appropriate for widespread use of CAR T cells.

From the foregoing, it would be desirable to develop an immunotherapy in which third-party, allogeneic cells could be pre-manufactured, characterized in detail, and available for immediate administration to patients. However, the use of allogeneic cells (i.e. cells obtained from different indi-viduals of the same species) raises some difficulties. In particular, allogeneic cells are susceptible to be rejected by the recipient's immune cells in a process termed host versus graft rejection (HvG), thus limiting their efficacy. More importantly, allogeneic cells may trigger a graft versus host disease (GvHD). Indeed, allogeneic T cells keep their endogenous T cell receptor (TCR) that can recognize the host tissue as foreign, resulting in GVHD which can lead to serious tissue damage and death. A current approach consists in the generation of universal CAR-T cells wherein endog-enous TCR is genetically inactivated (Qasim et al., Sci Trans) Med., 2017 Jan. 25, 9(374)). Other strategies are based on the use of immune cell populations that are less prone to alloreactivity, such as CAR-NK cells lacking endogenous TCR or CAR-NKT cells (Rotolo et al., Cancer Cell. 2018 Oct. 8; 34(4):596-610). However, the frequency of NKT cells in human blood is very low (0.01-0.5%).

Thus, alternative and/or improved allogeneic CAR-T cell-based immunotherapies are still needed.

SUMMARY OF THE INVENTION

The invention provides a mucosa associated invariant T (MATT) cell expressing a chimeric antigen receptor (CAR), for use in the treatment of a cancer, an immune disease or an infectious disease in a subject, wherein the MATT cell is allogenic with respect to the subject.

In a particular embodiment, the MATT cell expressing a chimeric antigen receptor (CAR) is for use in the treatment of a cancer.

The cancer can be a hematologic malignancy. In another particular embodiment, the cancer can be a solid tumor, preferably selected from the group consisting of breast cancer, prostate cancer, ovarian cancer, cervical cancer, skin cancer, pancreatic cancer, colorectal cancer, renal cancer, liver cancer, brain cancer, and lung cancer.

In one aspect, the CAR-MATT cell is to be administered to an immunocompromised subject. In particular, the CAR-MATT cell is to be administered after a conditioning treat-ment rendering the subject immunocompromised. The con-ditioning treatment can consist in chemotherapy, radiotherapy and/or lymphodepleting antibodies.

In a particular embodiment, the disease is a hematologic malignancy. In this embodiment the CAR-MATT cell is preferably administered prior to a transplant of hematopoi-etic stem cells (HSC) or right after a transplant of hema-topoietic stem cells (HSC).

In a particular embodiment, the cancer is a hematologic malignancy, such as leukemia, lymphoma or multiple myeloma, at a stage of minimal residual disease (MRD). Preferably, the MATT cell expresses a CAR that specifically binds to a tumor-associated antigen (TAA).

The TAA can be expressed at the surface of tumor cells. Preferably the TAA is CD19, GD2, EGFR, CD20, CD22, CD33, CD138, CD52, CD30, ROR1, HER2, EpCAM, MUC-1, MUC5AC, BCMA, CD38, SLAMF7/CS1, CD123, IL-13Ra2, HER2, LeY, MUC16 or PSMA. More preferably the TAA is CD19, CD20, CD22, CD33, CD138, BCMA, CD38, SLAMF7/CS1, IL-13Ra2 or HER2.

In another embodiment, the MATT cell expresses a CAR that specifically targets an intracellular oncoprotein or intra-cellular tumor-associated antigen in particular, WT-1, NY-ESO-1, MAGE, PRAME, RAS, mesothelin, c-Met, CEA, CSPG-4, EBNA3C, CA-125 or GPA7.

Carboxyfluorescein succinimidyl ester (CFSE)-labeled responder PBMCs were cultured with irradiated allogeneic PBMCs (1:1 ratio). Responder T cells were identified at the end of the 6-day culture by gating living cells and then on $CD3^+$ T cells. Proliferation of conventional CD3 T (Tconv) and $V\alpha7.2^+$ $CD161^{high}$ MATT cells was quantified by CFSE dilution (% of $CFSE^{low}$ cells). A) Representative CFSE staining gated on Tconv (left panels) and MATT cells (right panels) after 6-day culture in the presence of allogeneic (upper panels) or autologous (lower panels) PBMCs. Num-bers in the quadrants indicate the percentage of proliferating ($CFSE^{low}$) cells (horizontal bars) among the indicated popu-lation.

B) Individual values and means±SD of proliferating (CFSE$^{low}$) Tconv and MATT cells (n=6 experiments using different recipient/donor pairs). P value (paired t test) is indicated.

Figure 2:
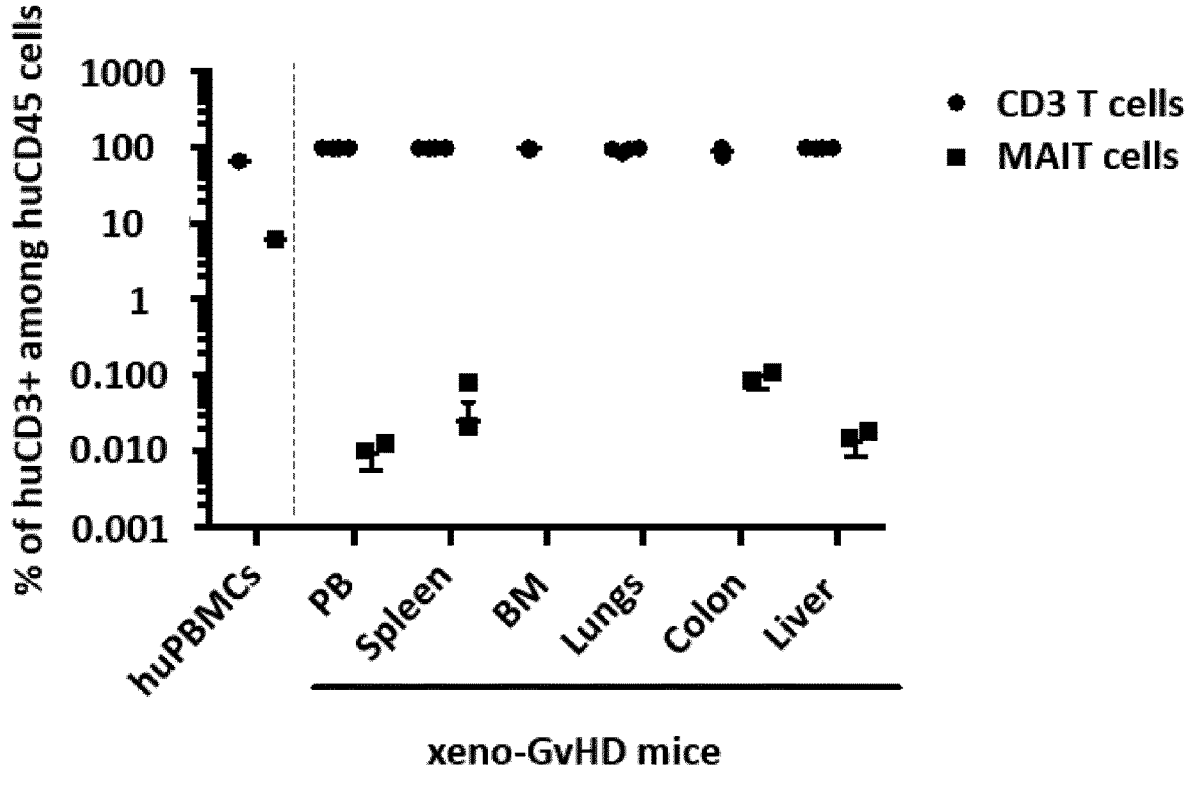

FIG. 2: MATT cells do not participate to GVHD induction in a humanized mouse model Irradiated (1.3 Gy) immunocompromised NOD-Scid-IL-2Rγ$^{null}$ (NSG) mice (n=3) were injected with $3×10^6$ human PBMCs, monitored to evaluate GVHD progression and euthanized when they exhibited >15% weight loss (±day 45). Graph shows the proportion of CD3 T cells and MATT cells among human (CD45+) leucocytes measured by flow cytometry in the initial inoculum (huPBMCs) and 45 days after transfer in peripheral blood (PB), spleen, bone marrow (BM), liver, colon, and lung of diseased mice.

FIG. 3: In vitro MATT cell expansion

PBMCs ($10^6$/ml) from healthy donors were cultured for 17 days in the presence of cytokines and synthetic MATT cell ligand. The percentage and absolute numbers of MATT cells were quantified by flow cytometry before (day 0) and at days 6, 10 and 17 of the culture period.

A) Representative staining of Va7.2$^+$ CD161$^{high}$ MATT cells (gated on CD3 T cells) over the culture period. Numbers indicate the percentage of MATT cells among CD3 T cells.

B) Expansion (fold change absolute number) of MATT cells over the culture period.

Figure 4:
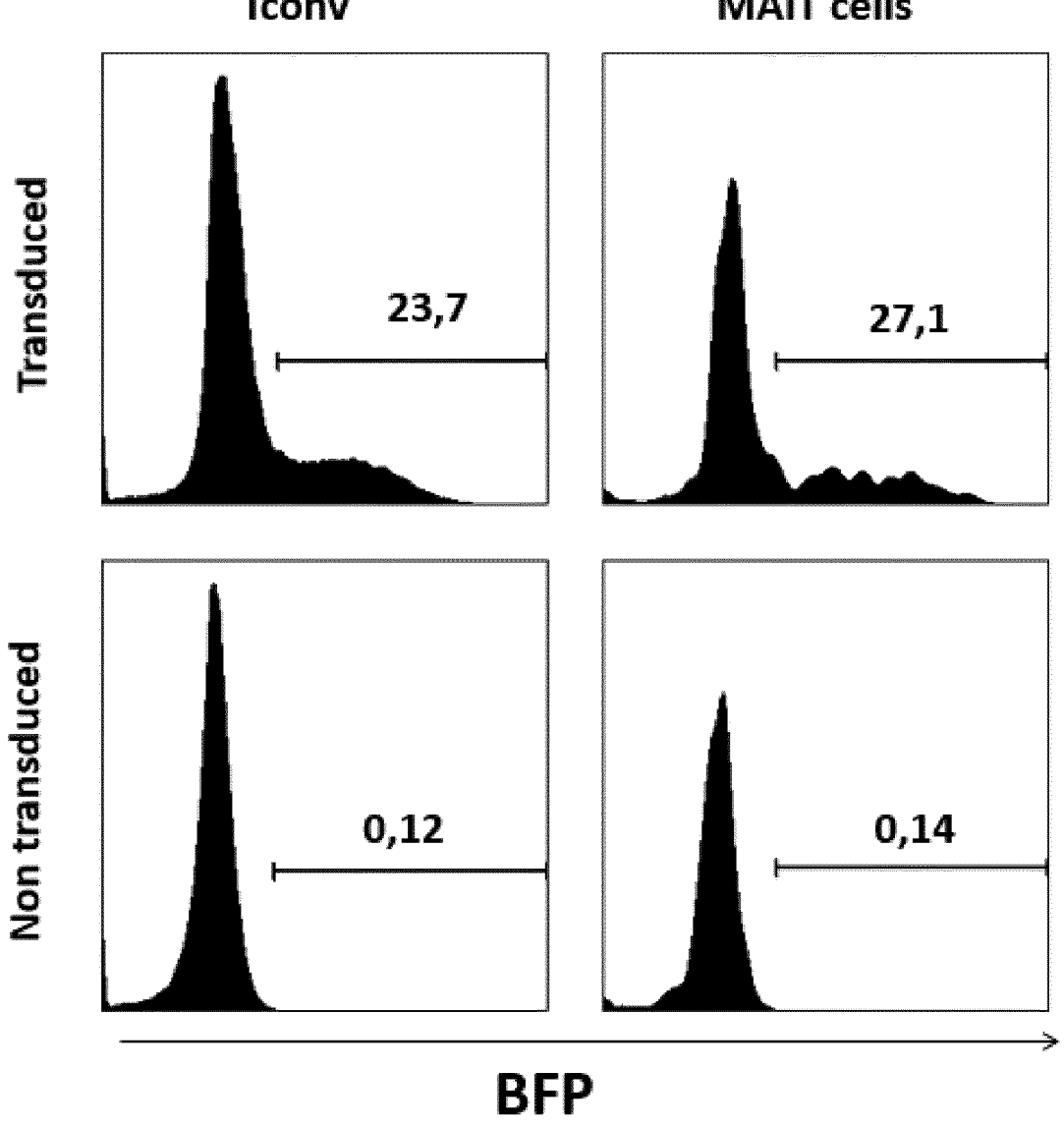

FIG. 4: Detection of CAR expression in MATT cells

Purified CD3 T cells were activated in vitro with anti-CD3/CD28 beads for 24 hours, and transduced with a lentiviral vector that encodes a CAR and a fluorescence reporter protein (BFP) to allow monitoring of CAR+ T cells. Surface expression of BFP among transduced (upper panel) or control non-transduced (lower panel) cells was determined 6 days later in conventional CD3 T cells and MATT cells. Numbers in the quadrants (horizontal bars) indicate the percentage of BFP+ cells among the indicated population.

DETAILED DESCRIPTION OF THE INVENTION

The present invention provides mucosa associated invariant T (MATT) cells expressing a chimeric antigen receptor (CAR), herein called CAR-MATT cells, for use in the field of allogeneic adoptive immunotherapy.

The CAR-MATT cells do not show any alloreactive potential; they do not proliferate in vitro in response to allogeneic cells and they do not participate to graft versus host disease (GvHD) induction, contrary to conventional T cells. According to the invention, CAR-MATT cells can be easily produced and expanded in vitro, in large volumes.

CAR-MATT cells can be stored, e.g. in frozen units, and are "ready to use", for a prompt administration to several recipients. Their preparation is cost-effective and they represent a universal treatment, regardless of the HLA disparity among subjects, and without risk of inducing GVHD.

Definitions

As used herein, the term "subject", "host", "individual," or "patient" refers to a mammal, preferably a human being, male or female at any age that is in-need of a therapy.

The terms "tumor-associated antigen", "TAA", "tumor antigen" and "cancer cell antigen" are used interchangeably herein. In each case, the terms refer to peptides, proteins, glycoproteins or carbohydrates that are specifically or preferentially expressed by cancer cells.

The term "Graft-Versus-Host Disease (GVHD)" refers to a common and serious complication wherein there is a reaction of donated immunologically competent lymphocytes against a transplant recipient's own tissues. GVHD is a possible complication of any transplant that uses or contains hematopoietic stem cells from either a related or an unrelated donor. "Treating" or treatment of a disease or condition refers to any act intended to ameliorate the health status of patients. "Treatment" can include, but is not limited to, alleviation or amelioration of one or more symptoms or conditions, diminishment of extent of disease, stabilization of the state of disease (e.g. maintaining a patient in remission), prevention of the disease or prevention of the spread of disease, delay or slowing of disease progression, amelioration or palliation of the disease state, diminishment of the reoccurrence of disease, and remission (whether partial or total). A treatment may include curative, alleviation or prophylactic effects. The term "prophylactic" may be considered as reducing the severity or the onset of a particular condition. "Prophylactic" also includes preventing reoccurrence of a particular condition in a patient previously diagnosed with the condition. "Therapeutic" may also reduce or delay the severity of an existing condition. Desirable effects of treatment include decreasing the rate of disease progression, ameliorating or palliating the disease state, and remission or improved prognosis. Alleviation can occur prior to signs or symptoms of the disease or condition appearing, as well as after their appearance. Thus, "treating" or "treatment" may include "preventing" or "prevention" of disease or undesirable condition. In one embodiment, treating a cancer includes inhibiting the growth or proliferation of cancer cells or killing cancer cells. In a particular embodiment, treating a cancer includes reducing the risk or development of metastasis. In another particular embodiment, treating a cancer may refer to the prevention of a relapse. Treating a cancer may also refer to maintaining a subject in remission.

As used herein, the terms "disorder" or "disease" refer to the incorrectly functioning organ, part, structure, or system of the body resulting from the effect of genetic or developmental errors, infection, poisons, nutritional deficiency or imbalance, toxicity, or unfavourable environmental factors. Preferably, these terms refer to a health disorder or disease e.g. an illness that disrupts normal physical or mental functions. More preferably, the term disorder refers to immune and/or inflammatory diseases that affect animals and/or humans. Preferably, the term disorder or disease refers to cancers, infectious diseases or immune diseases.

The term "cancer" as used herein is defined as disease characterized by the rapid and uncontrolled growth of aberrant cells. Cancer cells can spread locally or through the bloodstream and lymphatic system to other parts of the body.

The term "infectious diseases" refers to disorders caused by organisms, such as bacteria, viruses, fungi or parasites.

The term "immune disease" or "auto-immune disease", as used herein, refers to a condition in a subject characterized by cellular, tissue and/or organ injury caused by an immunologic reaction of the subject to its own cells, tissues and/or organs The CAR-MATT Cell The "CAR-MATT cell" of the invention designates a mucosa associated invariant T (MATT) cell expressing a chimeric antigen receptor (CAR).

Mucosal-associated invariant T (MATT) cells are a subset of nonconventional T cells. In humans, MATT cells are found in the blood, liver, and mucosae, defending against microbial activity and infection. MATT cells are characterized by a semi-invariant T cell receptor alpha (TCRα) chain (Vα 7.2-Jα 33/20/12 in humans), that can combine with a restricted number of possible TCRβ chains. This semi-invariant TCR is restricted by the monomorphic, highly conserved, MHC class-I related 1 (MR1) molecule. In contrast to conventional T cells that recognize classical MHC-peptide complexes, MATT cells recognize microbial-derived riboflavin precursor derivatives such as 5-OP-RU or 5-OE-RU, presented by MR1. Adult MATT cells are easily identified by flow cytometry as CD3+ CD4⁻Vα7.2+ CD161$^{high}$ (or IL-18a$^{high}$ or CD26$^{high}$) using the corresponding staining. Upon recognition of MR1 ligands, MATT cells release inflammatory cytokines (IFNγ, TNFα, IL-17) and mediate perforin-dependent cytotoxicity of target cells. MATT cells are preferentially localized in the liver and mucosae, including lung and intestine, and are also abundant in the adult peripheral blood (1-10% of T cells) while they are very few in cord blood (<0.1% of T cells).

The present invention relates to the use of MATT cells that are allogeneic, i.e. the cells are isolated and/or otherwise prepared from a subject other than the subject who is to receive or who ultimately receives the cell therapy. As used herein, the term "allogeneic" refers to cells or tissues obtained from different individuals of the same species, where the donor and recipient are not genetically identical. In some embodiments, the second subject expresses the same HLA genotype as the first subject. The CAR-MATT are shown to not mediate host tissue damage related to GVHD. As potent effector cells, CAR-MAITs are therefore useful as universal tools for adoptive immunotherapy in an allogeneic setting.

In the context of the present invention, the MATT cell is genetically modified to express a chimeric antigen receptor (CAR).

"Chimeric antigen receptors (CARS)," as used herein, refer to artificial T-cell receptors, chimeric T-cell receptors, or chimeric immunoreceptors, and encompass engineered receptors that graft an artificial specificity onto a particular immune effector cell, i.e. the MATT cell.

A CAR typically comprises an ectodomain (extracellular domain) and an endodomain (cytoplasmic domain), joined by a transmembrane domain. The ectodomain, expressed on the surface of the cell, comprises an antigen binding domain or receptor domain and optionally a spacer (or hinge) region linking the antigen binding domain to the transmembrane domain. The transmembrane domain is typically a hydrophobic alpha helix that spans across the lipid bilayer of the cell membrane. The endodomain of the CAR is composed of an intracellular signaling module that induces MATT cell activation upon antigen binding. The endodomain may include several signaling domains, as explained infra.

Antigen Binding Domain

The extracellular domain of the CAR comprises an antigen binding domain that specifically binds or recognizes a target antigen.

As used herein, "bind" or "binding" refer to peptides, polypeptides, proteins, fusion proteins and antibodies (including antibody fragments) that recognize and contact an antigen. Preferably, it refers to an antigen-antibody type interaction. By "specifically bind" it is meant that the antigen binding domain of the CAR recognizes a specific antigen, but does not substantially recognize or bind other molecules in a given sample. The "specific binding" is dependent upon the presence of a particular structure (e.g., an antigenic determinant or epitope). As used herein, the term "specific binding" means the contact between an antigen binding domain of the CAR and an antigen with a binding affinity of at least 10-6 M. In certain aspects, the antigen binding domain of the CAR binds with affinities of at least about 10-7 M, and preferably 10-8 M, 10-9 M, 10-10 M. The binding affinity can be measured by any method available to the person skilled in the art, in particular by surface plasmon resonance (SPR).

In one embodiment, such antigen binding domain is an antibody, preferably a single chain antibody. Preferably, the antibody is a humanized antibody. Particularly, such antigen binding domain is an antibody fragment selected from fragment antigen binding (Fab) fragments, F(ab')2 fragments, Fab' fragments, Fv fragments, recombinant IgG (rIgG) fragments, single chain antibody fragments, single chain variable fragments (scFv), single domain antibodies (e.g., sdAb, sdFv, nanobody) fragments, diabodies, and multi-specific antibodies formed from antibody fragments. In particular embodiments, the antibodies are single-chain antibody fragments comprising a variable heavy chain region and/or a variable light chain region, such as scFv. Particularly, such antigen binding domain is selected from a Fab and a scFv.

In embodiments wherein the antigen targeting domain is a scFv, the scFv can be derived from the variable heavy chain (VH) and variable light chain (VL) regions of an antigen-specific mAb linked by a flexible linker. The scFv retains the same specificity and a similar affinity as the full antibody from which it is derived. The peptide linker connecting scFv VH and VL domains joins the carboxyl terminus of one variable region domain to the amino terminus of the other variable domain without compromising the fidelity of the VHVL paring and antigen-binding sites. Peptide linkers can vary from 10 to 30 amino acids in length. In one embodiment, the scFv peptide linker is a Gly/Ser linker and comprises one or more repeats of the amino acid sequence Gly-Gly-Gly-Ser (SEQ ID NO: 1) or Gly-Gly-Gly-Gly-Ser (SEQ ID NO: 2).

The extracellular domain of the CAR may comprise one or more antigen binding domain(s).

In a particular embodiment, the CAR specifically binds to a tumor-associated antigen (TAA). In particular, the CAR specifically binds to any TAA expressed at the surface of tumor cells, preferably CD19, GD2, EGFR, CD20, CD22, CD33, CD138, CD52, CD30, ROR1, HER2, EpCAM, MUC-1, MUC5AC, BCMA, CD38, SLAMF7/CS1, CD123, IL-13Ra2, HER2, LeY, MUC16, PSMA, more preferably the TAA is CD19, CD20, CD22, CD33, CD138, BCMA, CD38, SLAMF7/CS1, IL-13Ra2 or HER2.

In a particular embodiment, the CAR specifically binds to CD19.

In another particular embodiment the CAR targets an intracellular oncoprotein or an intracellular tumor-associated antigen in particular WT-1, NY-ESO-1, MAGE, PRAME, RAS, mesothelin, c-Met, CEA, CSPG-4, EBNA3C, CA-125, GPA7. In particular, said intracellular oncoprotein or tumor-associated antigen are processed and expressed on the cell surface as peptides bound to histocompatibility (HLA) molecules.

In another particular embodiment, the CAR-MATT cell is for use in the treatment of an infectious disease. In this embodiment, the CAR can target a component of a pathogen expressed at the surface of infected cells, preferably the CAR targets a viral protein expressed on the cell surface, more preferably the CAR targets the HIV envelope protein.

In another particular embodiment, the CAR-MATT cell is for use in the treatment of an autoimmune disease. In this embodiment, the CAR preferably targets self-reactive antibodies expressed at the surface of autoimmune B cells, for example the CAR targets self-reactive antibodies directed to desmoglein 3 in pemphigus vulgaris.

Spacer or Hinge Domain

The CAR optionally comprises a spacer or hinge domain linking the antigen binding domain to the transmembrane domain.

In some embodiments, the CAR comprises a hinge sequence between the antigen binding domain and the transmembrane domain and/or between the transmembrane domain and the cytoplasmic domain. One ordinarily skilled in the art will appreciate that a hinge sequence is a short sequence of amino acids that facilitates flexibility.

In particular, the spacer or hinge domain linking the antigen binding domain to the transmembrane domain is designed to be sufficiently flexible to allow the antigen binding domain to orient in a manner that allows antigen recognition.

The hinge may be derived from or include at least a portion of an immunoglobulin Fc region, for example, an IgG1 Fc region, an IgG2 Fc region, an IgG3 Fc region, an IgG4 Fc region, an IgE Fc region, an IgM Fc region, or an IgA Fc region. In certain embodiments, the hinge domain includes at least a portion of an IgG1, an IgG2, an IgG3, an IgG4, an IgE, an IgM, or an IgA immunoglobulin Fc region that falls within its CH2 and CH3 domains.

Exemplary hinges include, but are not limited to, a CD8a hinge, a CD28 hinge, IgG1/IgG4 (hinge-Fc part) sequences, IgG4 hinge alone, IgG4 hinge linked to CH2 and CH3 domains, or IgG4 hinge linked to the CH3 domain, those described in Hudecek et al. (2013) Clin. Cancer Res., 19:3153, international patent application publication number WO2014031687, U.S. Pat. No. 8,822,647 or published app. No. U52014/0271635. As hinge domain, the invention relates to all or a part of residues 118 to 178 of CD8a (GenBank Accession No. NP_001759.3), residues 135 to 195 of CD8 (GenBank Accession No. AAA35664), residues 315 to 396 of CD4 (GenBank Accession No. NP 000607.1), or residues 137 to 152 of CD28 (GenBank Accession No. NP_006130.1) can be used. Also, as the spacer domain, a part of a constant region of an antibody H chain or L chain (CHI region or CL region) can be used. Further, the spacer domain may be an artificially synthesized sequence.

In some embodiments, for example, the hinge sequence is derived from a CD8 alpha molecule or a CD28 molecule.

Transmembrane Domain

The transmembrane domain of the CAR functions to anchor the receptor on the cell surface. The choice of the transmembrane domain may depend on the neighboring spacer and intracellular sequences.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 zeta, CD3 epsilon, CD3 gamma, CD3 delta, CD45, CD4, CD5, CD8, CD9, CD16, CD22, CD33, CD37, CD64, CD80, CD86, CD134, CD137, CD154, ICOS/CD278, GITR/CD357, NKG2D, and DAP molecules. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. A transmembrane domain is thermodynamically stable in a membrane. It may be a single alpha helix, a transmembrane beta barrel, a beta-helix of gramicidin A, or any other structure.

Optionally, a short oligo- or polypeptide linker, preferably between 2 and 10 amino acids in length may form the linkage between the transmembrane domain and the intracellular signaling domain(s) of the CAR. A glycine-serine doublet may provide a suitable linker.

Intracellular Domain

The terms "intracellular domain", "cytoplasmic domain" and "intracellular signaling domain" are used interchangeably herein. The role of the intracellular domain of the CAR is to produce an activation signal to the MATT cell as soon as the extracellular domain has recognized the antigen. In particular, the intracellular domain of the CAR triggers or elicits activation of at least one of the normal effector functions of the MATT cell.

Examples of intracellular domain sequences that are of particular use in the invention include those derived from an intracellular signaling domain of a lymphocyte receptor chain, a TCR/CD3 complex protein, an Fc receptor subunit, an IL-2 receptor subunit, CD3$\zeta$, FcR$\gamma$, FcR$\beta$, CD3$\gamma$, CD3$\delta$, CD3$\epsilon$, CD5, CD22, CD79a, CD79b, CD66d, CD278(ICOS), FcsRI, DAP10, and DAP12. It is particularly preferred that the intracellular domain in the CAR comprises a cytoplasmic signaling sequence derived from CD3c The intracellular domain of the CAR can be designed to comprise a signaling domain (such as the CD3 signaling domain) by itself or combined with costimulatory domain (s). A costimulatory molecule can be defined as a cell surface molecule that is required for an efficient response of lymphocytes to an antigen. Examples of such molecules include CD27, CD28, 4-1BB (CD137), OX40 (CD134), CD30, CD40, CD244 (2B4), ICOS, lymphocyte function-associated antigen-1 (LFA-1), CD2, CD7, LIGHT, NKG2C, B7-H3, and a ligand that specifically binds with CD83, CD8, CD4, b2c, CD80, CD86, DAP10, DAP12, MyD88, BTNL3, and NKG2D. The intracellular signaling portion of the above recited co-stimulatory domains can be used alone or in combination with other co-stimulatory domains. In particular, the CAR can comprise any combination of two or more co-stimulatory domains from the group consisting of CD27, CD28, 4-1BB (CD137), OX40 (CD134), CD30, CD40, CD244 (2B4), ICOS, LFA-1, CD2, CD7, LIGHT, NKG2C, B7-H3, and a ligand that specifically binds with CD83, CD8, CD4, b2c, CD80, CD86, DAP10, DAP12, MyD88, BTNL3, and NKG2D.

Thus, for example, the CAR can be designed to comprise a signaling domain such as the CD3$\zeta$ signaling domain and two co-stimulatory signaling domains selected from CD28 and CD40, CD28 and 4-1BB (CD137), CD28 and OX40 (CD134), and CD28 and LFA-1.

"First-generation CARs" contain a single signaling domain. CARs containing a signaling domain together with one additional costimulatory domain are termed "second generation" while those containing a signaling domain together with two additional costimulatory domains are listed as "third generation". For example, first-generation CARs contain solely the CD3 chain as a single signaling domain. Second- and third-generation CARs consist of one or two additional costimulatory signaling domains, respectively, such as CD28, CD27, OX-40 (CD134) and 4-1BB (CD137). For example, second-generation CAR may contain CD3 and CD28 signaling domains, while third-generation CAR may contain CD3c CD28 and either OX40 (CD134) or 4-1BB (CD137).

The CAR of the invention may be a first generation, a second generation, or a third generation CAR as described hereabove. Preferably, the CAR is a second or third generation CAR.

"TRUCKs" represent the recently developed 'fourth-generation' CARs. TRUCKs (T cells redirected for universal cytokine killing) are CAR-redirected T cells used as vehicles to produce and release a transgenic product that accumulates in the targeted tissue. The product, for example a pro-inflammatory cytokine, may be constitutively produced or induced once the T cell is activated by the CAR. Other substances such as enzymes or immunomodulatory molecules may be produced in the same way and deposited by CAR-redirected T cells in the targeted lesion. This strategy involves two separate transgenes expressing for example (i) the CAR and (ii) a cell activation responsive promoter linked to a cytokine such as IL-12. Consequently, immune stimulatory cytokine such as IL-12 is secreted upon CAR engagement.

In a particular embodiment, the CAR is a CAR of fourth generation as defined above.

In a particular embodiment, multiple CARs such as CARs binding to different antigens, may be expressed by a single MATT-cell.

CAR-MATT Cells Production

MATT Cell Acquisition

The production of CAR-MATT cells comprises a step of providing MATT cells from a cell culture or from a blood sample from an individual subject or from blood bank. MATT cells preferably derive from a donor subject, in particular a healthy donor subject.

The cells can be acquired from blood samples (including peripheral blood and cord blood) as well as samples resulting from one or more processing steps, such as separation, centrifugation, genetic engineering, washing, and/or incubation. In a particular embodiment, the sample from the donor comprises peripheral blood mononuclear cells (PBMCs).

In a particular embodiment, MATT cells are collected from any location in which they reside in the subject including, but not limited to peripheral blood, peripheral blood mononuclear cells (PBMCs), bone marrow, cord blood.

In a particular embodiment, the MATT cells are collected by apheresis, in particular by leukapheresis.

MATT Cell Isolation

As known to one of skill in the art, various methods are readily available for isolating immune cells from a subject or can be adapted to the present application, for example using Life Technologies Dynabeads® system; STEMcell Technologies EasySep™, RoboSep™, RosetteSep™, SepMate™; Miltenyi Biotec MACS™ cell separation kits, cell surface marker expression and other commercially available cell separation and isolation kits (e.g., ISOCELL from Pierce, Rockford, IL). MATT cells may be isolated through the use of beads or other binding agents available in such kits specific to MATT cell surface markers.

In some embodiments, the isolation is affinity- or immunoaffinity-based separation. For example, the isolation in some aspects includes separation of MAIT cells based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. Such separation steps can be based on positive selection, in which the MATT cells having bound the reagents are retained for further use, and/or negative selection, in which the MATT cells having not bound to the antibody or binding partner are retained. In some embodiments, multiple rounds of separation steps are carried out, where the positively or negatively selected fraction from one step is subjected to another separation step, such as a subsequent positive or negative selection.

In some embodiments, MATT cell population is collected and enriched via flow cytometry, in which cells stained for multiple cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the isolation of MATT cells is based on positive or high surface expression of CD3, CD8, Vα 7.2, CD161 CD26 and/or IL-18Ra (CD218a), and/or on the negative expression of CD4 and/or optionally on the presence of NKG2D or NKp30 receptors.

In a particular embodiment, the MATT cells are positively isolated using beads coated with an antibody, in particular an anti-Vα 7.2 antibody and an anti-IL18Ra or anti-CD161 or anti-CD26 antibody.

The isolated MATT cells may be used directly, or they can be stored for a period of time, such as by freezing.

MATT Cell Activation and Expansion

Whether prior to or after genetic modification of the MATT cells to express a desirable CAR, the cells can be activated and/or expanded. In some embodiments, the MATT cells are incubated in stimulatory conditions or in the presence of a stimulatory agent. Such conditions include those designed to induce proliferation, expansion, activation, and/or survival of MATT cells, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors and any other agents designed to activate the MATT cells.

For example, MATT cells can be incubated with an anti-CD3 antibody and/or an anti-CD28 antibody under conditions stimulating proliferation of the cells.

In some embodiments, the MATT cells of the invention can be expanded in vitro by co-culturing with tissue or cells. In some embodiments, the MATT cells are expanded by co-culturing with feeder cells, such as non-dividing PBMC. In some aspects, the non-dividing feeder cells can comprise irradiated PBMC feeder cells, in particular autologous or allogeneic irradiated PBMC.

In a particular embodiment, MATT cells are expanded in vitro by CD3/CD28 stimulation in presence of autologous or allogeneic irradiated PBMCs and IL-2, IL7, IL-12, IL-18 and/or IL-15 cytokines.

In a particular embodiment, MATT cells are expanded and/or activated in vitro in the presence of MATT cell activating ligands such as 5-OP-RU and/or 5-OE-RU.

In another particular embodiment, the method comprises a step of preferential in vitro MATT cell expansion from a cell sample of a donor, in particular from PBMCs of a donor. Preferential in vitro MATT cell expansion can be carried out by culturing PBMCs from a donor in the presence of synthetic 5-OP-RU, and optionally with cytokines. In particular, PBMCs from a donor are cultured in the presence of 5-OP-RU and IL-2 (such as rhuIL-2).

In a particular embodiment the MATT cells are preferably ex vivo expanded for at least about 5 days, preferably not less than about 10 days, more preferably not less than about 15 days and most preferably not less than about 20 days before administration to the patient. In another embodiment the MATT cells have been expanded at least about 100 fold, preferably at least about 200 fold, and more preferably at least about 400 fold, preferably at least about 600 fold, more preferably at least about 1000 fold and even more preferably at least about 1500 fold compared to day 0 of expansion, before administration to a patient.

In some embodiments, the method of preparation includes steps for freezing, e.g., cryopreserving, the cells, either before or after isolation, incubation, and/or engineering.

Cell Transduction and Selection

In certain embodiments, MATT cells are transduced in order to express one or more CAR.

It is contemplated that a nucleic acid construct encoding the CAR can be introduced into the MATT cells as naked DNA or in a suitable vector.

Naked DNA generally refers to the DNA encoding a chimeric receptor contained in a plasmid expression vector in proper orientation for expression. Physical methods for introducing a nucleic acid construct into a host cell include calcium phosphate precipitation, lipofection, particle bombardment, microinjection, electroporation, and the like. Other means can be used including colloidal dispersion systems, such as macromolecule complexes, nanocapsules, microspheres, beads, and lipid-based systems including oil-in-water emulsions, micelles, mixed micelles, and liposomes.

In a particular embodiment, the nucleic acid construct encoding the CAR is introduced into the MATT cell by a viral vector such as retroviruses, adenoviruses, adeno-associated viruses, herpesviruses and lentiviruses. In particular, the vector is a lentiviral vector.

On order to confirm the presence of the CAR sequence in the MATT cell, a variety of assays may be performed. Such assays include, for example, "molecular biological" assays well known such as Southern and Northern blotting, RT-PCR and quantitative PCR; "biochemical" assays, such as detecting the presence or absence of a particular peptide; "immunological" assays, such as detecting expression of the CAR at the cell surface by flow cytometry.

Pharmaceutical Composition

It is further described a pharmaceutical or veterinary composition comprising the CAR-MAIT cell as described hereabove.

The pharmaceutical composition may additionally comprise a pharmaceutically acceptable carrier. An "acceptable carrier" as referred to herein, is any known compound or combination of compounds that are known to those skilled in the art to be useful in formulating pharmaceutical or veterinary compositions. In a specific embodiment, the term "pharmaceutically acceptable" means approved by a regulatory agency of the Federal or a state government or listed in the U.S. or European Pharmacopeia or other generally recognized pharmacopeia for use in animals, and humans.

The term "carrier" refers to a diluent, adjuvant, excipient, or vehicle with which the CAR-MATT cell is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. In a further aspect, the pharmaceutical or veterinary composition may comprise one or more population of MATT-cells, wherein each population expresses a different CAR.

The pharmaceutical or veterinary composition can be formulated for any conventional route of administration including a parenteral, intravenous, intramuscular, subcutaneous administration and the like.

When administered parenterally, the pharmaceutical or veterinary composition is preferably administered by intravenous route of administration.

Desirably, a pharmaceutically acceptable form is employed which does not adversely affect the desired immune potentiating effects of CAR-MATT cells.

The pharmaceutical or veterinary composition contains the CAR-MATT cells in amounts effective to treat or prevent the disease or condition, such as a therapeutically effective or prophylactically effective amount. The desired amount can be delivered by a single administration of the composition, by multiple administrations of the composition, or by continuous administration of the composition. The amount of CAR-MATT cells to be administered can be determined by standard procedure well known by those of ordinary skills in the art. Physiological data of the patient (e.g. age, size, weight and health and weight of the recipient, kind of concurrent treatment, if any, frequency of treatment and the nature of the effect desired) and the routes of administration have to be taken into account to determine the appropriate dosage, so as a therapeutically effective amount will be administered to the patient.

Uses

The invention relates to a CAR-MATT for use in the treatment of a disease in a subject, wherein the MATT cell is allogenic with respect to the subject.

In a preferred embodiment, the CAR-MATT cells of the invention are used as a therapeutic product, ideally as an "off the shelf" product.

In one aspect, the disease or disorder to be treated is a condition selected from a proliferative disease or disorder, preferably cancer; an infectious disease or disorder, preferably a viral, bacterial or fungal infection; an inflammatory disease or disorder; and an immune disease or disorder, preferably autoimmunity or autoimmune diseases.

In a particular embodiment, the CAR-MATT cell and/or the pharmaceutical composition are suitable for treatment of viral infections such as HIV infection, hepatitis A, B or C virus infections, herpes virus infection (e.g. VZV, HSV-1, HSV-6, HSV-II, CMV, and EBV) and influenza virus infection. Non-viral examples may include chronic fungal diseases such Aspergillosis, Candidiasis, Coccidioidomycosis, and diseases associated with *Cryptococcus* and Histoplasmosis. None limiting examples of chronic bacterial infectious agents may be *Chlamydia pneumoniae, Listeria monocytogenes*, and *Mycobacterium tuberculosis*. Infectious diseases also include sexually transmitted diseases (e.g., *Chlamydia*, gonorrhea), diphtheria or cholera.

In a particular embodiment, the CAR-MAIT cell and/or the pharmaceutical composition are suitable for treatment of autoimmune disorders. Autoimmune disorders can affect almost every organ system in the subject including, but not limited to, diseases of the nervous, gastrointestinal, and endocrine systems, as well as skin and other connective tissues, eyes, blood and blood vessels. Examples of auto-immune diseases include, but are not limited to Pemphigus vulgaris, Hashimoto's thyroiditis, Systemic lupus erythema-tosus, Sjogren's syndrome, Graves' disease, Scleroderma, Rheumatoid arthritis, Multiple sclerosis, Myasthenia gravis and Diabetes.

In a particular embodiment, the CAR-MAIT cell and/or the pharmaceutical composition is for use in the treatment of a cancer. Accordingly, the present invention also relates to methods for inhibiting the growth of a cancer in a subject in need thereof and/or preventing cancer formation and/or spread of the cancer in a patient in need thereof.

In a particular embodiment, the CAR-MATT cell is for use in the treatment of the relapse of the cancer.

In particular, the cancer is a solid tumor or a hematopoi-etic cancer.

In particular, the cancer is a solid tumor, such as sarcomas and carcinomas, including fibrosarcoma, myxosarcoma, liposarcoma, chondrosarcoma, osteosarcoma, and other sar-comas, synovioma, mesothelioma, Ewing's tumor, leiomyo-sarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocar-cinoma, sweat gland carcinoma, medullary thyroid carci-noma, papillary thyroid carcinoma, pheochromocytomas sebaceous gland carcinoma, papillary carcinoma, papillary adenocarcinomas, medullary carcinoma, bronchogenic car-cinoma, renal cell carcinoma, hepatoma, bile duct carci-noma, choriocarcinoma, Wilms' tumor, cervical cancer, tes-ticular tumor, seminoma, bladder carcinoma, melanoma, and CNS tumors (such as a glioma (such as brainstem glioma and mixed gliomas), glioblastoma (also known as glioblas-toma multiforme) astrocytoma, CNS lymphoma, germi-noma, medulloblastoma, Schwannoma craniopharyogioma, ependymoma, pinealoma, hemangioblastoma, acoustic neu-roma, oligodendroglioma, menangioma, neuroblastoma, ret-inoblastoma and brain metastases).

Hematopoietic cancers are cancers of the blood or bone marrow. Examples of hematological (or hematogenous) cancers include leukemias, including acute leukemias (such as acute lymphoid leukemia, acute myelocytic leukemia, acute myeloid leukemia and myeloblastic, promyelocytic, myelomonocytic, monocytic and erythroleukemia), chronic leukemias (such as chronic myelocytic (granulocytic) leu-kemia, chronic myeloid leukemia, and chronic lymphoid leukemia), polycythemia vera, lymphoma, Hodgkin's dis-ease, non-Hodgkin's lymphoma (indolent and high grade forms), multiple myeloma, Waldenstrom's macroglobuline-mia, heavy chain disease, myelodysplastic syndrome, hairy cell leukemia and myelodysplasia.

In a particular embodiment, the disease is a hematologic malignancy, more preferably leukemia, lymphoma or myeloma.

In a particular embodiment, the MATT cell is to be administered to an immunocompromised subject. In immu-nocompetent hosts, allogeneic cells may be rejected by the host immune system. Thus, to prevent rejection of alloge-neic CAR MATT cells, the host's immune system is pref-erably effectively suppressed or compromised.

In particular, the CAR-MATT cell is administered after a conditioning treatment rendering the subject immunocom-promised.

In particular, the conditioning treatment is a myeloabla-tive or non-myeloablative treatment, or a lymphodepleting chemotherapy.

In particular, the conditioning treatment consists in chemo-therapy and/or radiotherapy and/or lymphodepleting anti-bodies.

Immunosuppressive agents may be used during the con-ditioning treatment, such as azathioprine, methotrexate, 5-fluoro-uracile, cyclophosphamide, fludaribine, pentosta-tin, romidepsin (FR901228), anti-CD52 (CAMPATH, alemtuzumab), anti-CD3, anti-CD20 (rituximab) antibody or other antibody therapies, cyclosporin, FK506, rapamycin, mycophenolic acid, steroids.

In a particular embodiment, the disease is a hematologic malignancy and the MATT cell is to be administered prior a transplant of hematopoietic stem cells (HSC) or right after a transplant of hematopoietic stem cells (HSC).

In particular, the CAR-MATT cell is for use in the treatment of a hematologic malignancy, at a stage of mini-mal residual disease (MRD).

Minimal Residual Disease (MRD) refers to cancer cells, in particular leukemic cancer cells, left in the body after treatment and constituting the major cause of relapse. In particular, the term minimal residual disease (MRD) is used to describe the low-level disease which is not detectable by conventional cytomorphology (see e.g. Briiggemann and Kotrova; Blood Advances 2017 1:2456-2466).

In particular, the CAR-MATT cells are used to eliminate the residual leukemic or disseminated tumor cells during a therapeutic window. CAR-MATT cells can be used as a bridge to transplant in patients with hematologic malignan-cies, or as treatment of minimal residual disease (MRD) or relapse (or adjuvant therapy for high-risk patients) after hematopoietic stem cell transplantation.

The administration of the CAR-MATT cells may be carried out in any convenient manner, including by injection, transfusion, implantation or transplantation. The composi-tions described herein may be administered to a patient by intravenous injection or intratumorally, intranodally or intra-peritoneally. In one embodiment, the cell compositions are preferably administered by intravenous injection.

EXAMPLES

Material and Methods
Flow Cytometry

Peripheral blood mononuclear cells from healthy donors were isolated by Ficoll density gradient centrifugation (Eu-robio) and used immediately or frozen. Multiparametric 10-color flow cytometry analyses were performed using combinations of the following antibodies for 15 min at 4° C.: anti-CD45 Krome Orange, anti-CD3 ECD, anti-CD8β PE or ECD, anti-TCR Vα24 PE Cy7 (all from Beckman Coulter); anti-TCR Vα7.2 FITC or APC (clone 3C10), anti-CD161 PerCP Cy5.5 or BV421, anti-CD4 AF700 (Biolegend); anti-CD161 APC, anti-CD3 APC Vio770 (Miltenyi Biotec); anti-CD4 APC AF750 (Invitrogen); anti-CD3 PerCP (BD Biosciences); Zombie aqua live/dead (BioLegend). Data were acquired on a Navios flow cytometer (Beckman Coulter) collecting a total of at least 100,000 events in a live gate. Gates were defined through isotype and fluorescence minus one (FMO) stains. The gating strategy was CD45 versus side scatter and MATT cells were defined as CD3+ CD4− CD161high Vα7.2+ T cells. Absolute cell counts were calculated on the same sample using CountBright Absolute Counting Beads (Invitrogen). Data were analyzed using FlowJo software.

Mixed Lymphocyte Reaction

Responder PBMCs were labeled with 1 µM Carboxyfluorescein succinimidyl ester (CFSE); $2\times10^5$ CFSE-labeled responder cells were cultured with or without $2\times10^6$ irradiated allogeneic or autologous (negative control) PBMCs in flat-bottom 96-well plates for 6 days. Responder T cells were identified at the end of the culture period by gating on living CD3+ cells. Proliferation of conventional T (Tconv) and MATT cells was quantified by CFSE dilution (% CFSE$^{low}$ cells).

Adoptive Transfer of Xenogeneic Cells

NSG mice (Jackson laboratory, Bar Harbor, MI) were housed in the pathogen-free animal facility of Institut de Recherche Saint-Louis (Paris). Eight- to 10-week-old female NSG were irradiated (1.3 Gy) 24 hours prior to injection of $3\times10^6$ human PBMCs in the caudal vein. Mice were assessed for survival daily, and weighed weekly. Development of acute GVHD was monitored based on weight loss, posture (hunching) and reduced mobility. Mice were sacrificed when weight loss was >15% (mean±45 days). Peripheral blood, spleen, bone marrow, liver, lungs and intestine were harvested. Tissues were subjected to mechanical dissociation, and single-cell suspensions were filtered through a cell stainer (70 µm, BD Biosciences). The proportion of CD3 T cells and MATT cells among human (CD45+) leucocytes was determined by flow cytometry in the initial inoculum and 45 days after transfer.

In Vitro MATT Cell Expansion

Healthy volunteer PBMCs ($10^6$/ml) were seeded in round-bottom 96-wells and cultured in RPMI-10% human serum in the presence of 300 nM synthetic 5-OP-RU (produced at Institut Curie by chemical synthesis of 5-A-RU (F. Shmidt, chemistry department) that was then mixed with methyglyoxal at the same molarity) and 100 IU/mL IL-2. After 6 days cells were counted and assessed for viability and MATT cell numbers by flow cytometry as described above. Cells were propagated with 100 nM 5-OP-RU and 100 IU/mL IL-2 every 3-4 days for up to 17 days.

MATT Cell Transduction

CD3 T cells were immunomagnetically purified from PBMC (human CD3+ T Cell Isolation Kit, Miltenyi Biotec), activated with anti-CD3/CD28 beads (1:1 ratio, Dynabeads Human T-Activator CD3/CD28, ThermoFisher Scientific) for 24 hours, and transduced with a lentiviral vector that encodes a CAR directed to a tumor antigen and a fluorescence reporter protein (blue fluorescent protein, BFP) to allow monitoring of CAR+ T cells. Cells were resuspended in fresh X-VIVO™ 15 medium (Lonza) supplemented with 5% human serum and 100 IU/mL IL-2. Transduction efficiency was determined 6 days later by flow cytometry as percentage of BFP+ cells among conventional CD3 T cells and MATT cells.

In Vitro CAR-MATT Cell Efficacy $5\times10^4$ luciferase-expressing tumor cells expressing the antigen targeted by the CAR were incubated with FACS-sorted CAR-T cells, CAR-MATT cells or mock-transduced MATT cells at various E/T ratios in 96-well microplate for 24 hours. Target cell viability was quantified by measurement of luminescence intensity.

Results

1. MATT Cells do not Proliferate In Vitro in Mixed Lymphocyte Reaction (MLR).

Figures 1A, 1B:
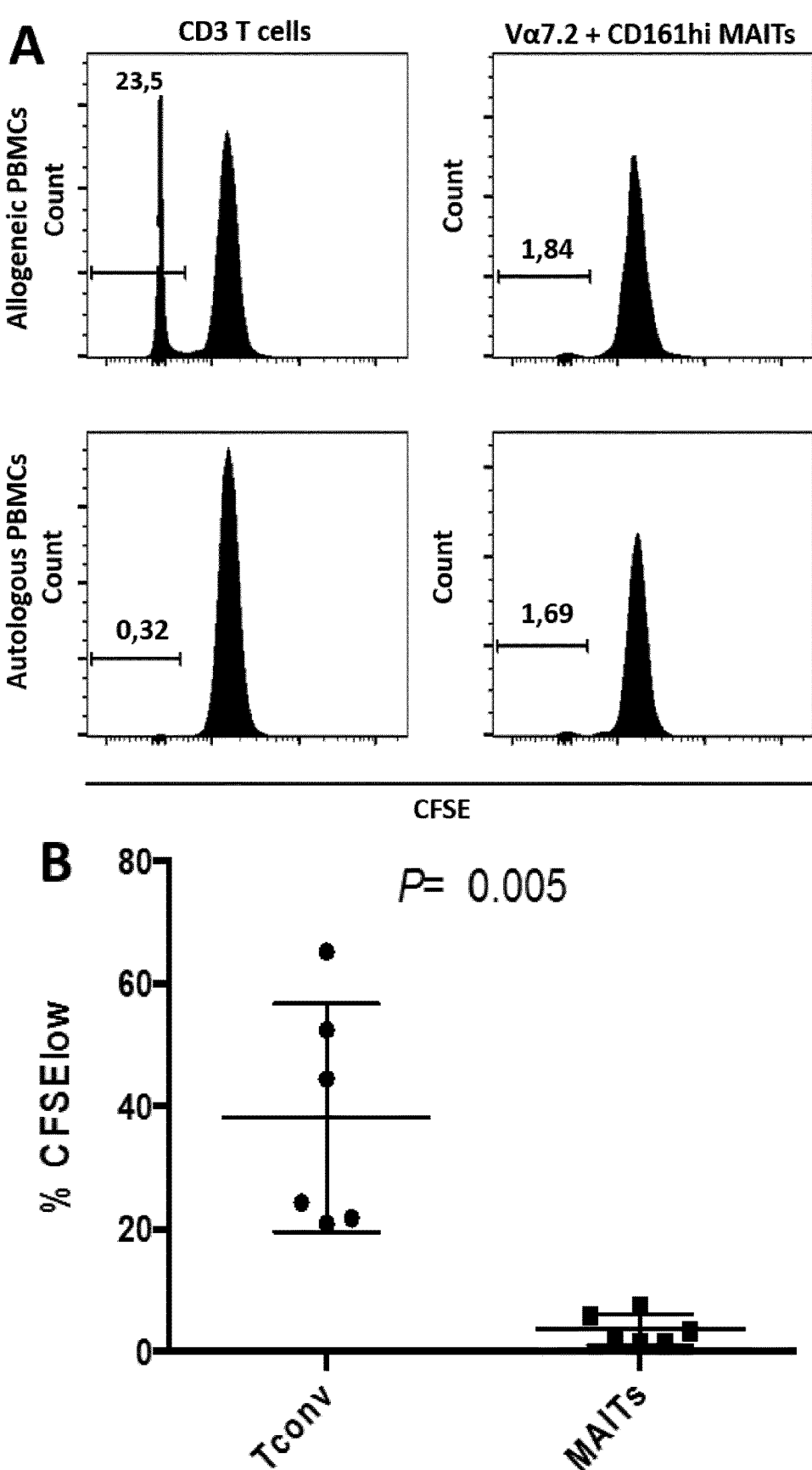
FIG. 1: MATT cells do not proliferate in vitro in response to allogeneic peripheral blood mononuclear cells (PBMCs).

To investigate the in vitro potential of MATT cells to recognize allogeneic cells and contribute to the alloimmune response, we used a flow-cytometry based MLR method to quantify MATT cell proliferation in the presence of third-party allogeneic cells. As shown in FIG. 1 (A and B), MATT cells showed no or minimal proliferation in response to allogeneic cells, at contrast with conventional CD3 T cells.

2. MATT Cells do not Participate to GVHD Induction in a Humanized Mouse Model.

To investigate the in vivo potential of MATT cells to contribute to acute GVHD, we used the transfer of human PBMCs in irradiated immunocompromised NOD-Scid-IL-2Rγnull (NSG) mice (FIG. 2). In this model, engraftment, expansion and activation of human T lymphocytes in a xenogeneic and lymphopenic environment leads to symptoms of acute xenogeneic-GVHD (±day 45 after transplant), with infiltration of human cells in various tissues, and ultimately death.

Irradiated (1,3 Gy) NSG mice injected with $3.10^6$ human PBMCs were monitored to evaluate GVHD progression (weight loss, hunched posture, ruffled fur, reduced mobility) and sacrificed when weight loss was >15% (mean 45 days after transfer). Flow cytometry analyses of human CD45+ leucocytes in the peripheral blood, spleen, bone marrow, liver, colon, and lung of diseased mice failed to detect the presence of MAITs, at contrast with massive accumulation of conventional CD3 T cells (FIG. 2).

Taken together, these results indicate that MAITs have low alloreactive potential and pave the way to use MATT cells as a source of lymphocytes for the development of universal allogeneic CAR-T cells.

3. Efficient MATT Cell Expansion and Lentiviral CAR Transduction

Figures 3A, 3B:
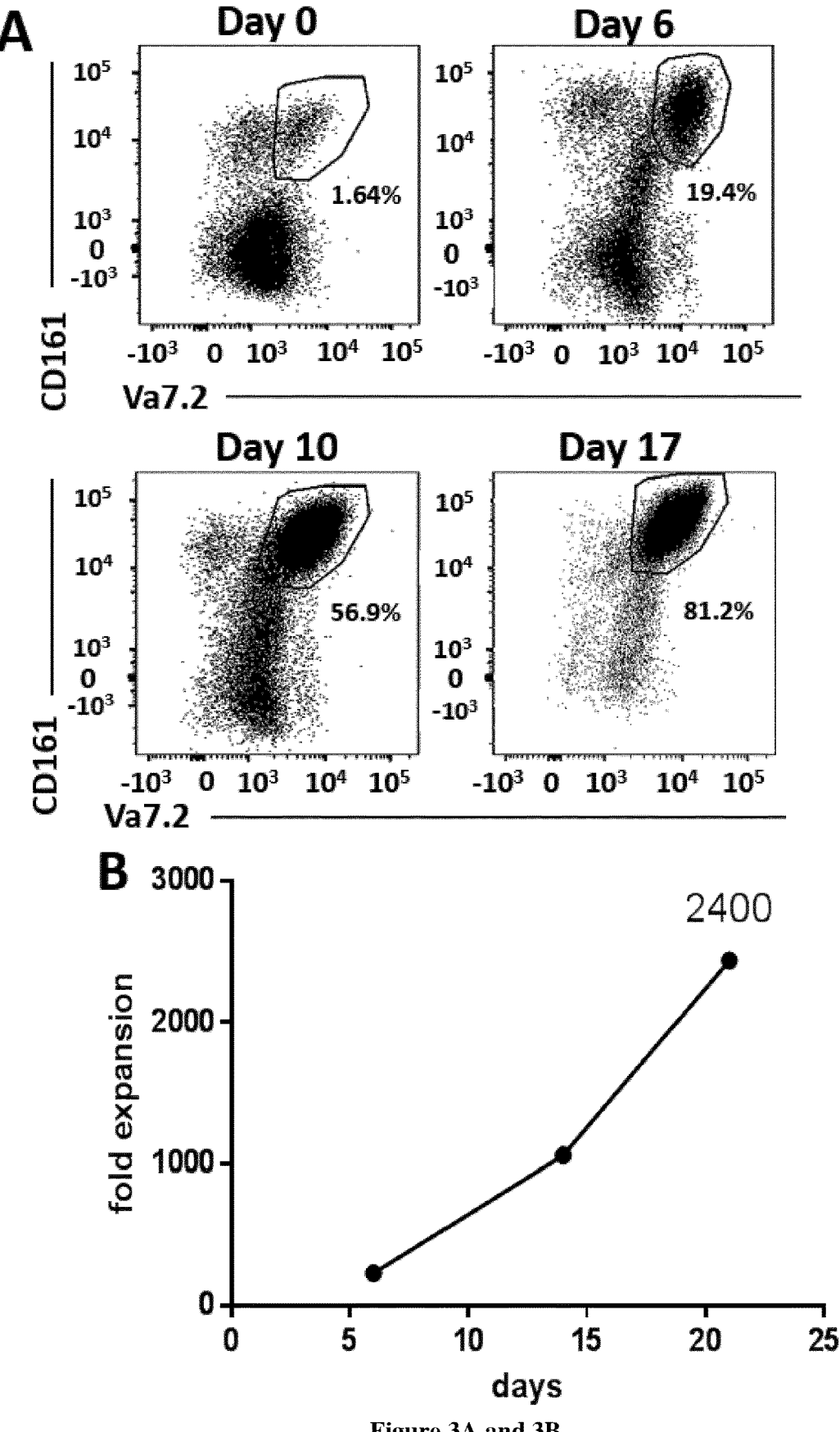

A prerequisite for using MATT cells as a new source of CAR-T cells is that MATT cells are able to expand in vitro in sufficient quantity, and can be efficiently transduced by a lentiviral vector. We established experimental conditions for preferential in vitro MATT cell expansion from healthy donor's PBMCs. Repeated stimulation with 5-OP-RU and IL-2 over a period of 21 days resulted in preferential enrichment of MATT cells (more than 80% of MATT cells among CD3 T cells at day 21) and 2400-fold expansion of absolute numbers of MATT cells over the culture period (FIGS. 3A and B).

Independently from the MATT cell expansion procedure, we also determined that lentiviral CAR transduction of MATT cells was as efficient as that of conventional CD3 T cells. As shown in FIG. 4 anti-CD3/CD28-stimulated CD3 T cells transduced with CAR-BFP lentivirus contained GFP+ MATT cells in a proportion similar to that of CD3 T cells.

4. CAR-MATT Cells Kill Relevant Target Cells as Efficiently as CAR-T Cells

To demonstrate the in vitro efficacy of CAR-MATT cells, we performed killing experiments against tumor cells expressing the relevant CAR target. $5\times10^4$ luciferase-expressing target cells were incubated with CAR-MATT, CAR-T or non-transduced MATT (NT) effector cells at various effector/target (E/T) ratios for 24 hours. Target cell viability was quantified by measurement of luminescence intensity (living target cells). CAR-MATT cells, but not non-transduced MATT cells (NT), killed tumor targets as efficiently as conventional CAR-T cells at low E:T ratio.

The invention claimed is:

1. A method of treating a cancer, an autoimmune disease or an infectious disease in a subject in need thereof, comprising administering to the subject a therapeutically effective amount of mucosa associated invariant T (MAIT) cells expressing a chimeric antigen receptor (CAR), wherein the MAIT cells are transduced in order to express the CAR, and wherein the MAIT cells are allogenic with respect to the subject and do not induce graft versus host disease in the subject.

2. The method according to claim 1, wherein the cancer is a hematologic malignancy.

3. The method according to claim 1, wherein the cancer is a solid tumor.

4. The method according to claim 1, wherein the subject is an immunocompromised subject.

5. The method according to claim 1, wherein the MAIT cells are administered after a conditioning treatment, rendering the subject immunocompromised.

6. The method according to claim 5, wherein the conditioning treatment is chemotherapy, radiotherapy and/or administration of lymphodepleting antibodies.

7. The method according to claim 1, wherein the CAR specifically binds to a tumor-associated antigen (TAA).

8. The method according to claim 1, wherein the CAR specifically binds to a TAA expressed at the surface of tumor cells.

9. The method according to claim 1, wherein the CAR specifically targets an intracellular oncoprotein, a self-reactive antibody, or an intracellular tumor-associated antigen.

10. The method according to claim 3, wherein the cancer is selected from the group consisting of: breast cancer, prostate cancer, ovarian cancer, cervical cancer, skin cancer, pancreatic cancer, colorectal cancer, renal cancer, liver cancer, brain cancer, and lung cancer.

11. The method of claim 1, wherein the MAIT cells are administered prior to a transplant of hematopoietic stem cells (HSC) or after a transplant of hematopoietic stem cells (HSC).

12. The method of claim 8, wherein the TAA is selected from the group consisting of CD19, GD2, EGFR, CD20, CD22, CD33, CD138, CD52, CD30, ROR1, HER2, EpCAM, MUC-1, MUC5AC, BCMA, CD38, SLAMF7/CS1, CD123, IL-13Ra2, LeY, MUC16 and PSMA.

13. The method of claim 12, wherein the TAA is CD19, CD20, CD22, CD33, CD138, BCMA, CD38, SLAMF7/CS1, IL-13Ra2 or HER2.

14. The method of claim 9, wherein the intracellular tumor-associated antigen is WT-1, NY-ESO-1, MAGE, PRAME, RAS, mesothelin, c-Met, CEA, CSPG-4, EBNA3C, CA-125 or GPA7.

15. The method of claim 1, further comprising activating the MAIT cells in the presence of a stimulatory agent prior to the administering step, wherein the stimulatory agent is not 5-OP-RU.

16. The method of claim 1, wherein the method is for treating an autoimmune disease.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Synthetic Gly / Ser linker

<400> SEQUENCE: 1

Gly Gly Gly Ser
1

<210> SEQ ID NO 2
<211> LENGTH: 5
<212> TYPE: PRT
<213> ORGANISM: artificial
<220> FEATURE:
<223> OTHER INFORMATION: Synthetic Gly / Ser linker

<400> SEQUENCE: 2

Gly Gly Gly Gly Ser
1               5
```